US006663628B2

(12) United States Patent  (10) Patent No.: US 6,663,628 B2
Peters  (45) Date of Patent: Dec. 16, 2003

(54) SURGICAL MICRO-RESECTING INSTRUMENT WITH ELECTROCAUTERY FEATURE

(75) Inventor: Gary F. Peters, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/961,543

(22) Filed: Sep. 24, 2001

(65) Prior Publication Data
US 2002/0038122 A1 Mar. 28, 2002

Related U.S. Application Data
(60) Provisional application No. 60/235,212, filed on Sep. 24, 2000.

(51) Int. Cl.[7] ............................................. A61B 18/18
(52) U.S. Cl. ............................ 606/45; 48/170; 48/49
(58) Field of Search .......................... 606/1, 41, 45, 606/46, 48–50, 167, 170, 171, 180; 604/21, 22

(56) References Cited

U.S. PATENT DOCUMENTS

| 4,368,734 A |   | 1/1983  | Banko               |         |
|-------------|---|---------|---------------------|---------|
| 4,530,356 A |   | 7/1985  | Helfgott et al.     |         |
| 4,760,317 A |   | 7/1988  | Hetzel et al.       |         |
| 4,850,354 A |   | 7/1989  | McGurk-Burleson et al. | |
| 4,986,825 A |   | 1/1991  | Bays et al.         |         |
| 5,195,959 A |   | 3/1993  | Smith               |         |
| 5,217,457 A |   | 6/1993  | Delahuerga et al.   |         |
| 5,364,395 A | * | 11/1994 | West, Jr.           | 606/46  |
| 5,707,402 A |   | 1/1998  | Heim                |         |
| 5,730,752 A |   | 3/1998  | Alden et al.        |         |
| 5,782,795 A |   | 7/1998  | Bays                |         |
| 5,797,907 A |   | 8/1998  | Clement             |         |
| 5,810,809 A | * | 9/1998  | Rydell              | 606/49  |
| 5,904,681 A | * | 5/1999  | West, Jr.           | 606/41  |
| 5,904,698 A |   | 5/1999  | Thomas et al.       |         |
| 5,908,419 A |   | 6/1999  | Hahnen et al.       |         |
| 5,913,857 A |   | 6/1999  | Ritchart et al.     |         |
| 5,922,003 A | * | 7/1999  | Anctil et al.       | 606/170 |
| 5,925,040 A |   | 7/1999  | Nardella et al.     |         |
| 5,941,876 A |   | 8/1999  | Nardella et al.     |         |

(List continued on next page.)

FOREIGN PATENT DOCUMENTS

| DE | 196 41 563 A1 | 10/1996 |
| DE | 196 41 564 A1 | 10/1996 |
| DE | 299 14 180 U1 | 8/1999  |
| GB | 2205045       | 11/1988 |

OTHER PUBLICATIONS

A copy of PCT International Search Report relating to PCT/US01/29730 mailed on Mar. 5, 2002 (9 pages).

(List continued on next page.)

Primary Examiner—Michael Peffley
(74) Attorney, Agent, or Firm—Curtis Kinghorn; Timothy A. Czaja

(57) ABSTRACT

A surgical micro-resecting instrument including an outer tubular member, an inner tubular member, a hub assembly, wiring, and an electrical insulator. The outer tubular member is formed of an electrically conductive material and defines a proximal section, a distal section forming a cutting window, and an internal lumen. The inner tubular member is disposed within the lumen and defines a proximal end and a distal end forming a cutting tip. The hub assembly maintains the outer tubular member and the inner tubular member. The wiring is permanently electrically connected to the proximal section of the outer tubular member with the electrical connection being encompassed by the hub assembly. The electrical insulator covers a region of the outer tubular member distal the hub assembly, at least the cutting window free of the insulator. In one preferred embodiment, the hub assembly includes an outer hub insert molded to the outer tubular member, and forms a generally radially extending shroud.

50 Claims, 5 Drawing Sheets

U.S. PATENT DOCUMENTS

| | | | |
|---|---|---|---|
| 5,951,548 A | | 9/1999 | DeSisto et al. |
| 5,951,551 A | | 9/1999 | Erlich |
| 5,957,881 A | | 9/1999 | Peters et al. |
| 6,007,533 A | * | 12/1999 | Casscells et al. ............. 606/45 |
| 6,022,362 A | | 2/2000 | Lee et al. |
| 6,032,673 A | * | 3/2000 | Savage et al. .............. 128/898 |
| 6,193,715 B1 | * | 2/2001 | Wrublewski et al. ......... 606/45 |
| 6,346,107 B1 | * | 2/2002 | Cucin .......................... 606/49 |
| 6,451,017 B1 | * | 9/2002 | Moutafis et al. .............. 606/41 |

OTHER PUBLICATIONS

A copy of PCT International Search Report mailed on Feb. 13, 2002 (8 pages).

XoMed Product Release, "RAD 55® & RAD 60 X-TREME®"; Sep. 1998.

Charles M. Myer, III, M.D. et al., "Use of a Laryngeal Micro Resector System", pp. 1165–1166; Jul. 1999.

Michael Friedman, M.D. et al., "A Safe, Alternative Technique for Inferior Turbinate Reduction", pp. 1834–1837; Nov. 1999.

XoMed Product Release, "SKIMMER™ Angle–Tip Laryngeal Blades" 1 page; ©1998.

XoMed Advertisement, "Lose the Laser", 2 pages; Aug. 1998.

Daniel G. Becker, M.D., "Technical Considerations in Powered Instrumentation", Otolaryngologic Clinics of North America, vol. 30, No. 3, pp. 421–433; Jun. 1997.

* cited by examiner

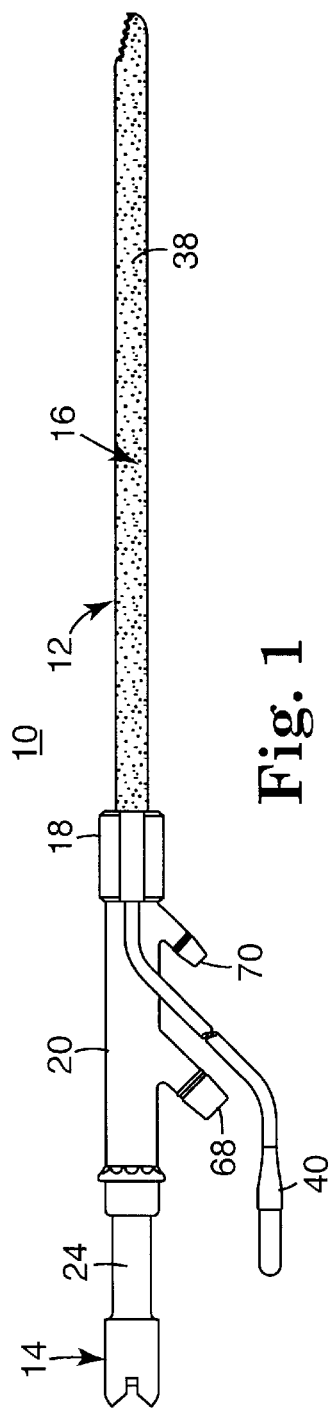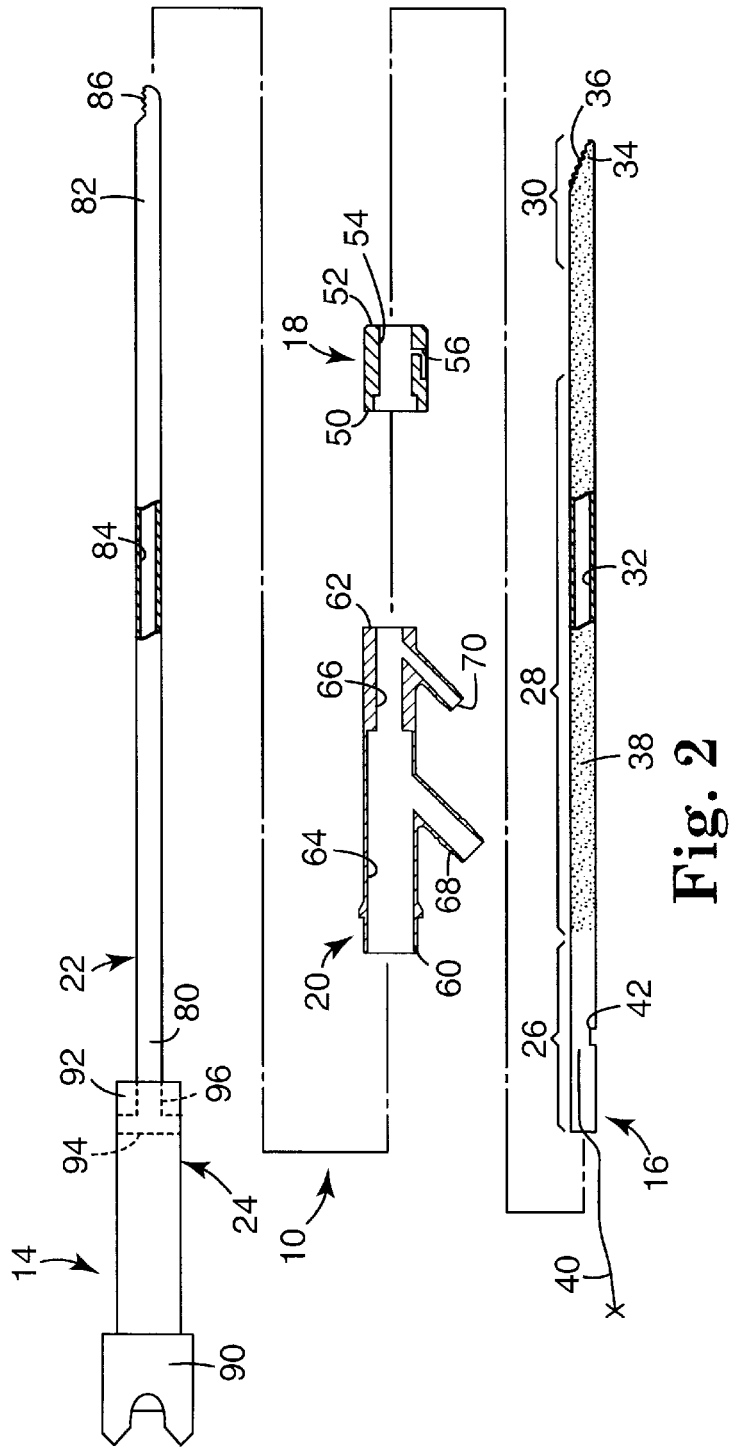

US 6,663,628 B2

SURGICAL MICRO-RESECTING INSTRUMENT WITH ELECTROCAUTERY FEATURE

CROSS-REFERENCE TO RELATED APPLICATIONS

This application claims the benefit of, and incorporates herein by reference an entirety of, U.S. Provisional application Ser. No. 60/235,212, filed Sep. 24, 2000.

BACKGROUND OF THE INVENTION

The present invention relates generally to surgical micro-cutting instruments. More particularly, it relates to a surgical micro-resecting instrument integrating both mechanical and electrical current cutting.

Surgical cutting instruments in which an elongate inner member is rotated within an elongate outer tubular member have become well accepted in surgical procedures where access to the surgical site is gained via a narrow portal or passage. Typically, the outer tubular member includes a distal end with an opening defining a cutting port or window, and the inner member includes a distal end forming a cutting tip for cutting bodily tissue at the window. Proximal ends of the inner and outer members are commonly secured to hubs that, in turn, are attached to a powered handpiece for rotating and/or oscillating the inner member relative to the outer tubular member. The cutting tip of the inner member can have various configurations specific to the surgical procedure in question (e.g., cutting, resecting, abrading, shaving, etc.), with the cutting window being suitably configured to cooperate with the particular configuration of the cutting tip. Often, the inner member is tubular so that the loose tissue resulting from a cutting, resecting, or abrading procedure can be aspirated through the hollow lumen of the inner member. With specific reference to ENT (i.e., ear, nose, and throat) applications, such as ethmoidectomy, sinus surgery, adenoidectomy, laryngeal surgery, etc., extremely sharp, micro-resecting blades or cutting tips are typically employed to effectuate the desired procedure.

The above-described surgical instruments rely upon a mechanical cutting action to resect, cut, shave, abrade, etc. the tissue in question. With respect to ENT procedures, mechanical-type, micro-resecting instruments are highly viable, and present distinct advantages over other available devices. For example, $CO_2$ lasers are available. However, laser-based systems are expensive and present the distinct risk of thermal trauma or burns.

Efforts have been made to improve upon the design of surgical micro-resecting instruments. For example, the blade or cutting tip configuration can be optimized for certain applications. Further, so as to facilitate access to certain bodily areas, the surgical cutting instrument has been modified from a generally straight form to one having a fixed- or variable-angle design.

Often times, during an ENT micro-resecting procedure, it is necessary to coagulate or otherwise stem bleeding at the target site to provide homostasis. The accepted technique for effectuating homostasis is to remove the micro-resecting instrument and deploy a suction coagulation device. While necessary, this technique is highly time consuming.

Surgical micro-resecting blade instruments continue to be extremely useful. However, a separate device is still required to achieve homostasis at the surgical site. Therefore, a need exists for a single surgical micro-resecting instrument capable of resecting tissue and provide homostasis.

SUMMARY OF THE INVENTION

One aspect of the present invention provides a surgical micro-resecting instrument including an outer tubular member, an inner tubular member, a hub assembly, wiring, and an electrical insulator. The outer tubular member is formed of an electrically conductive material and defines a proximal section, an intermediate section, a distal section, and an internal lumen. Further, the distal section forms a cutting window that is otherwise open to the lumen. The inner tubular member is disposed within the lumen and defines a proximal end and a distal end. In this regard, the distal end forms a cutting tip. The hub assembly maintains the outer tubular member at the proximal section thereof, and the inner tubular member at the proximal end thereof. The wiring is permanently, electrically connected to the proximal section of the outer tubular member. Additionally, the wiring is adapted to deliver energy to the outer tubular member from a remote power source. In this regard, the electrical connection of the wiring to the outer tubular member is encompassed by the hub assembly. Finally, the electrical insulator covers a region of the outer tubular member distal the hub assembly. More particularly, at least the cutting window is free of the insulator. With this configuration, the cutting tip is available for resecting tissue. When necessary, an electrical current is applied to the proximal section of the outer tubular member via the wiring. The insulator insulates the outer tubular member along the intermediate section and at least a portion of the distal section, thereby providing an electrode surface area at the exposed portion thereof. As a result, the exposed portion of the distal section cauterizes contacted tissue via the energy to achieve homostasis. In one preferred embodiment, the insulator is a dielectric material coated onto the outer tubular member. In another preferred embodiment, the hub assembly includes an outer hub insert molded to the outer tubular member, and forms a generally radially extending shroud.

Yet another aspect of the present invention relates to a surgical micro-resecting system for use in ENT procedures. The system includes a micro-resecting instrument, a powered surgical handpiece, and an energy source. The micro-resecting instrument includes an outer tubular member, an inner tubular member, a hub assembly, wiring, and an electrical insulator. The outer tubular member is formed of an electrically conductive material and includes a distal section and an internal lumen, with the distal section forming a cutting window otherwise open to the lumen. The inner tubular member is disposed within the lumen of the outer tubular member and defines a distal end forming a cutting tip. The hub assembly is connected to, and maintains, the outer tubular member and the inner tubular member. The wiring is permanently electrically connected to the proximal section of the outer tubular member, with the connection between the wiring and the outer tubular member being encompassed by the hub assembly. Finally, the electrical insulator covers a region of the outer tubular member distal the hub assembly, with at least the cutting window being free of the insulator. The powered surgical handpiece is coupled to a proximal end of the inner tubular member and is configured to drive the inner tubular member relative to the outer tubular member as part of a micro-resecting procedure. Finally, the energy source is electrically connected to the wiring opposite the outer tubular member. With this configuration, activation of the powered surgical handpiece initiates resecting of tissue. Additionally, activation of the energy source effectuates tissue cauterization via delivery of energy to the region of the outer tubular member not otherwise covered by the insulator. In one preferred embodiment, the powered surgical handpiece and the energy source are operated by switching devices located remote of the micro-resecting instrument.

Yet another aspect of the present invention relates to a method for performing a micro-resecting operation at a target site of a patient as part of an ENT surgical procedure. The method includes providing a micro-resecting instrument including an outer tubular member, an inner tubular member, wiring, a hub assembly, and an electrical insulator. The outer tubular member has a lumen and a distal section forming a cutting window otherwise open to the lumen. The inner tubular member is disposed within the lumen and has a distal end forming a cutting tip. The wiring is permanently electrically connected to a proximal section of the outer tubular member at a connection point. The hub assembly is connected to, and maintains, the inner and outer tubular members and envelops the connection point. The electrical insulator covers a region of the outer tubular member distal the hub assembly, such that at least the cutting window remains exposed relative to the insulator. The distal section of the outer tubular member is delivered to the target site such that the cutting window is located at the target site and the cutting tip is located within the cutting window. The inner tubular member is driven relative to the outer tubular member such that the cutting tip resects tissue at the target site to effectuate a portion of an ENT procedure. Energy is applied to an exposed region of the outer tubular member via the wiring. Finally, tissue at the target site is cauterized via the energized exposed region of the outer tubular member.

Yet another aspect of the present invention relates to a method of manufacturing a micro-resecting instrument for use in ENT procedures. The method includes providing an outer tubular member formed of an electrically conductive material and including a proximal section, a distal section, and a lumen. In this regard, the distal section is formed to include a cutting window open to the lumen. An inner tubular member is also provided. The inner tubular member has a proximal end and a distal end, with the distal end forming a cutting tip. The inner tubular member is disposed within the lumen of the outer tubular member such that the cutting tip is aligned with the cutting window. Wiring is electrically connected to the proximal section of the outer tubular member. A hub assembly is connected to the proximal section of the outer tubular member and the proximal end of the inner tubular member. In this regard, the hub assembly is positioned to encompass the connection between the wiring and the outer tubular member such that the wiring is permanently, electrically connected to the outer tubular member. Finally, a region of the outer tubular member distal the hub assembly is covered with an electrical insulator. In this regard, at least the cutting window remains exposed relative to the insulator. In one preferred embodiment, the method further includes providing the hub assembly to include an inner hub for connection to the inner tubular member and an outer hub for connection to the outer tubular member, with the outer hub being insert molded to the outer tubular member.

BRIEF DESCRIPTION OF THE DRAWINGS

FIG. 1 is a side view of a surgical micro-resecting instrument in accordance with the present invention;

FIG. 2 is an exploded side view of the micro-resecting instrument of FIG. 1, with portions illustrated in cross-section;

DESCRIPTION OF THE PREFERRED EMBODIMENTS

Figure 3:
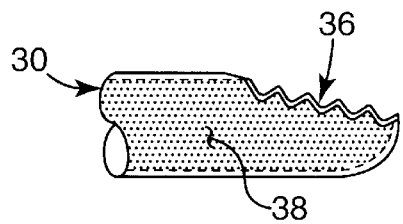
FIG. 3 is an enlarged side view of a distal portion of the outer tubular member shown in FIG. 2.

One preferred embodiment of a surgical micro-resecting instrument or blade 10 in accordance with the present invention is illustrated in FIG. 1. The surgical instrument 10 includes an outer blade member or assembly 12 and an inner blade member or assembly 14. The inner blade assembly 14 is coaxially received within the outer blade assembly 12. The components 12, 14 are described in greater detail below. In general terms, however, the outer blade assembly 12 includes an outer tubular member 16, a cap 18, and an outer hub 20. The inner blade assembly 14 includes an inner tubular member 22 (illustrated in FIG. 2) and an inner hub 24. The outer hub 20 secures and maintains the inner tubular member 22 relative to the outer tubular member 16. To this end, a portion of the inner hub 24 is sealed within the outer hub 20 (such as by seal rings as described below), and is configured for attachment to a surgical handpiece (not shown). As made clear below, the outer hub 20, the inner hub 22 and the cap 18 serve as a hub assembly for maintaining the outer tubular member 16 and the inner tubular member 22.

With additional reference to the exploded view of FIG. 2, the outer tubular member 16 is similar to outer tubular members employed with conventional tissue micro-resecting instruments, and is formed as an elongated tube. More particularly, the outer tubular member 16 defines a proximal section 26, an intermediate section 28, and a distal section 30. A lumen 32 extends from a cutting window 34, otherwise formed at the distal section 30, to the proximal section 26. The proximal section 26 is configured for mounting to the outer hub 20, whereas the distal section 30 forms a cutting surface or edge 36 about at least a portion of the cutting window 34.

The outer tubular member 16 is preferably formed of a relatively rigid, electrically conductive material such as 304 stainless steel. In addition, an outer surface of the intermediate section 28 and the distal section 30 is coated or covered with a dielectric insulation material (shown generally at 38 in FIG. 2). Importantly, the proximal section 26 is preferably free of the dielectric insulation coating 38. The dielectric coating 38 insulation material is preferably a nylon coating, but other known dielectric materials may also be employed. In one preferred embodiment, the dielectric coating 38 has a thickness in the range of approximately 0.010–0.014 inch, more preferably 0.012 inch. Further, as shown best by the enlarged view of FIG. 3, in one embodiment, the dielectric coating or electrical insulator 38 is not applied to, or does not cover, the cutting surface 36 formed at the distal section 30. Because the cutting surface or edges 36 are free of the dielectric coating 38, an electrical energy, such as radio frequency (RF) energy, otherwise applied to the proximal section 26 (FIG. 2) propagates to the surface 36 for subsequent interaction (e.g., electrocauterization) with contacted tissue (not shown). For example, and returning to FIG. 2, a wire conductor 40 or wiring is preferably fused to the proximal section 26 (otherwise free of the dielectric coating 38). Thus, in a preferred embodiment the wiring 40 is permanently electrically connected to the outer tubular member 16. The wire conductor 40 is further connected at an opposite end to an electrical current supply (not shown). Activation of the electrical current supply produces an electrical energy at the cutting surface 36. Notably, tissue or other structures otherwise in contact with the outer tubular member 16 at locations other than the cutting surface 36 (e.g., the intermediate section 28 and the distal section 30) are not affected by the applied current due to the dielectric coating 38. The dielectric coating 38 can assume a variety of other electrical insulator forms that otherwise cover a desired region of the outer tubular member 16. For example, the electrical insulator can be a sheath covering the outer tubular member 16.

As described in greater detail below, the electrical insulator 38 can be adapted to cover even less of the distal section 30. For example, an outer surface 42 (referenced generally in FIG. 3, it being understood that in the view of FIG. 3, the outer surface 42 is encompassed by the insulator 38) of the distal section 30 opposite the cutting surface 36 (or cutting window 34) can be free of, or otherwise left exposed by, the electrical insulator 38.

Other than the preferred dielectric coating or insulator 38 described above, the outer tubular member 16 can assume a wide variety of forms. For example, the outer tubular member 16 can be substantially straight, or may form one or more bends that facilitate use of the instrument 10 at different surgical sites. Examples of an outer tubular member incorporating one or more bends is provided, for example, in U.S. Pat. No. 5,922,003, the teachings of which are incorporated herein by reference. In addition, the outer tubular member 16 can be sized such that the inner tubular member 22, described below, is fixed within the outer tubular member 16, or provide for rotation and/or oscillation of the inner tubular member 22 relative to the outer tubular member 16. In one preferred embodiment, the outer tubular member 16 is sized to allow rotation and/or oscillation, as well as to provide a path for internal irrigation. To this end, and as described in greater detail below, the outer tubular member 16 preferably has an inner diameter slightly greater than an outer diameter of a corresponding portion of the inner tubular member 22, and defines an irrigation inlet 42. In one preferred embodiment, the outer tubular member 16 has an outer diameter of 4 mm and an overall length of approximately 4.312 inches, with the proximal section 26 having a length of approximately 0.86 inches. Other dimensions, either greater or smaller, are equally acceptable.

Figure 4:
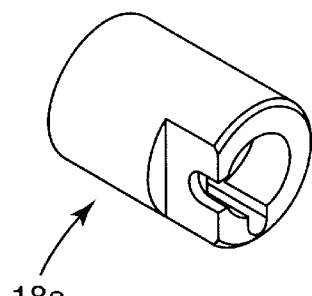
FIG. 4 is an enlarged, perspective view of an alternative embodiment cap useful with the instrument of FIG. 1.

For ease of illustration, the cap 18 is depicted in cross-section in FIG. 2. The cap 18 is configured for placement over the proximal section 26 of the outer tubular member 16 and defines a proximal end 50, a distal end 52, a central passage 54, and a slot 56. The cap 18 is formed of a non-conductive material, such as acrylonitrile butadiene styrene (ABS) plastic. The central passage 54 is sized to frictionally receive and maintain the outer tubular member 16. Further, the central passage 54 at the distal end 52 is sized to engage a portion of the outer hub 20, and thus is preferably stepped. The slot 56 is formed along a side of the cap 18 and preferably extends through the proximal end 50. With this in mind, the cap 18 is configured such that upon final assembly, the cap 18 encompasses that portion of the proximal section 26 of the outer tubular member 16 otherwise extending from the outer hub 20, thereby providing a transition from the outer hub 20 to the dielectric coating 38 and protecting the wire conductor 40. To this end, the slot 56 is sized to receive and guide a portion of the wire conductor 40 outwardly relative to the outer hub 20. The cap 18 can assume forms other than that specifically illustrated in FIG. 2. For example, an alternative embodiment cap 18a is shown in FIG. 4. In another alternative embodiment, and as described in greater detail below, the cap 18 can be eliminated where the outer hub 20 is over-molded (i.e., insert molded) to the outer tubular member 16.

For ease of illustration, the outer hub 20 is depicted in cross-section in FIG. 2. The outer hub 20 is configured to retain the outer tubular member 16 and the inner blade assembly 14. In this regard, the outer hub 20 is an elongated body defining a proximal end 60, a distal end 62, a proximal passage 64, a distal passage 66, an aspiration port 68, and an irrigation port 70. The proximal passage 64 extends from the proximal end 60 and is sized to receive a portion of the inner hub 24. Further, the proximal passage 64 is fluidly connected to the aspiration port 68. The distal passage 66 is fluidly connected to, and extends from, the proximal passage 64, terminating at the distal end 62. The irrigation port 70 is fluidly connected to the distal passage 66. As described below, the distal passage 66 is sized in accordance with an outer diameter of the outer tubular member 16 such that the outer tubular member 16 is rigidly coupled to the outer hub 20 upon final assembly. Further, a position of the irrigation port 70 corresponds with the position of the irrigation inlet 42 formed by the outer tubular member 16 such that upon final assembly, the irrigation inlet 42 is aligned with the irrigation port 70. As described below, then, the outer hub 20 provides both an irrigation path for internal blade irrigation and also an aspiration path for the aspiration of fluids and tissues during use.

The inner tubular member 22 is connected to, and extends distally from, the inner hub 24 and is sized to be coaxially disposed within the outer tubular member 16. The inner tubular member 22 defines a proximal end 80, a distal end 82, and a central lumen 84 extending therebetween. The distal end 82 forms a cutting tip 86 that is optimally configured to perform a desired resecting or shaving procedure as is known in the art. In one embodiment, the inner tubular member 22 is formed of a uniform, rigid material, such as 304 stainless steel. Alternatively, the inner tubular member 22 can be configured to effectuate bending of the inner tubular member 22, such as by a flexible coupling (not shown). Examples of available flexible coupling configuration are described, for example, in U.S. Pat. No. 5,922,003, the teachings of which are incorporated herein by reference.

The inner hub 24 is an elongated body defining a proximal portion 90 and a distal portion 92. The proximal portion 90 is configured to releasably secure the surgical micro-resecting instrument 10 to a handpiece (not shown), and may include a coupling device such as a spring (not shown). The distal portion 92 is sized to be slidably received within the proximal passage 64 formed by the outer hub 20 and forms a radial passage 94 and a longitudinal passage 96. The longitudinal passage 96 is sized to receive and maintain the proximal end 80 of the inner tubular member 22. The radial passage 94 is in fluid communication with the longitudinal passage 96, and is generally aligned with the aspiration port 68 upon final assembly. With this configuration, then, fluids and other materials can be drawn through the central lumen 84 of the inner tubular member 22 via the aspiration port 68.

Figure 5:
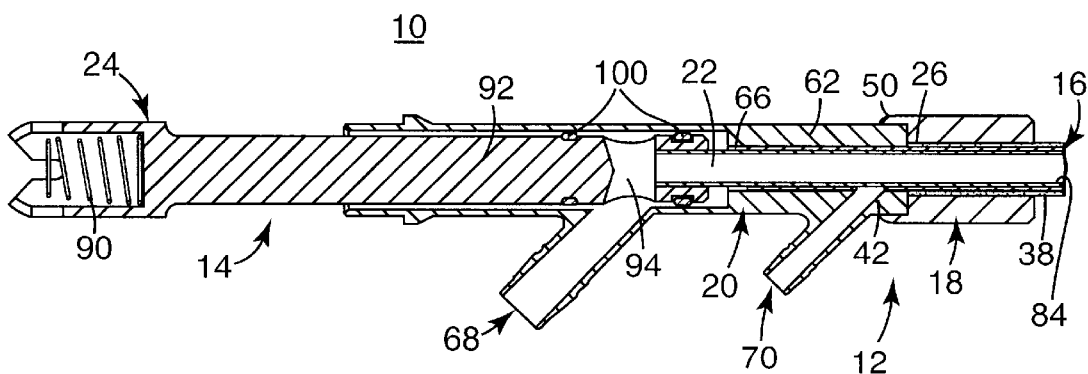
FIG. 5 is an enlarged, cross-sectional view of a portion of the surgical instrument of FIG. 1.

Assembly of the micro-resecting instrument 10 is best shown with reference to FIG. 5. For ease of illustration, the wire conductor 40 (FIGS. 1 and 2), otherwise fused to the proximal section 26 of the outer tubular member 16, is not depicted in FIG. 5. As previously described, the outer tubular member 16 is preferably coated with the dielectric coating 38 (shown generally in FIG. 5), it being recalled that the proximal section 26 is free of the dielectric coating 38. Notably, however, the connection point of the wiring 40 and the outer tubular member 16 is preferably encompassed by the cap 18 or other portion of the hub assembly. With this configuration, the micro-resecting instrument 10 does not include any direct switching devices for selectively electrically connecting the wiring 40 and the outer tubular member 16. Instead, a switch (such as a foot switch) remote of the instrument 10 is preferably employed. In other words, the power source and related activation device is located proximal or upstream of the instrument 10 for activating/stopping delivery of energy to the wiring 40 and thus the instrument 10. With this in mind, FIG. 5 illustrates the cap 18 being secured over the outer tubular member 16 at the proximal section 26 as shown. Further, the wire conductor 40 (not shown) is guided through the slot 56 (not shown) formed by the cap 18.

The proximal section 26 of the outer tubular member 16 is then assembled to the distal end 62 of the outer hub 20. In particular, the proximal end 50 of the cap 18 is secured over the distal end 62 of the outer hub 20, and the proximal section 26 of the outer tubular member 16 partially secured within the distal passage 66 of the outer hub 20. As shown upon final assembly, the irrigation inlet 42 of the outer tubular member 16 is aligned with the irrigation port 70 of the outer hub 20.

The inner blade assembly 14 is then coaxially disposed within the outer blade assembly 12. In particular, the inner tubular member 22 is coaxially placed within the outer tubular member 16. Further, the distal portion 92 of the inner hub 24 is coaxially placed within the outer hub 20. In this regard, seal rings 100 are positioned proximal and distal the radial passage 94 to seal the radial passage 94 of the inner hub 24 relative to the aspiration port 68 of the outer hub 20. The seal ring 100 also seal the aspiration port 68 relative to the irrigation port 70. As described below, the instrument 10 is configured to provide internal irrigation, and presents an opportunity for fluid flow directly from the irrigation port 70 to the aspiration port 68. The seal rings 100 prevent this from occurring, such that irrigation fluid must flow to the distal end 82 (FIG. 2) of the tube 22 for target site application.

The preferred assembly depicted in FIG. 5 provides an aspiration fluid path that is external from a handpiece (not shown) that is otherwise releasably connected to the proximal portion 90 of the inner hub 24 and the proximal end 60 pf the outer hub 20 (described below). More particularly, during use, a vacuum placed over the aspiration port 68 draws or aspirates fluids and/or tissues at the surgical site from the distal end 82 (FIG. 2) of the inner tubular member 22 through the aspiration port 68 via the central lumen 84. This preferred construction effectively isolates the handpiece from possibly becoming an electrically conductive path when saline or other fluid is being aspirated from the surgical site. Alternative configurations effectuating this same design characteristic are described, for example, in U.S. Pat. No. 5,957,881, the teachings of which are incorporated herein by reference. Similarly, an external irrigation fluid path is provided via the irrigation port 70 being fluidly connected to a spacing otherwise generated between an outer diameter of the inner tubular member 22 and an inner diameter of the outer tubular member 16.

As is clear from the above, the cap 18, the outer hub 20, and the inner hub 24 combine to serve as a hub assembly for the instrument 10, the dielectric coating or insulator 38 covering a region of the outer tubular member 16 distal the hub assembly (e.g., distal the cap 18 in FIG. 5). Where the insulator 38 is something other than a dielectric coating (e.g., a sheath), the insulator 38 can be assembled to the hub assembly co-axially about the outer tubular member 16, again extending distal the hub assembly. Regardless, the instrument 10, and in particular the hub assembly, is preferably characterized by the absence of any switches for controlling driving of the inner tubular member 22 and/or selectively electrically connecting the wiring 40 to the outer tubular member 16. These operations are controlled via switching devices (e.g., footswitch) located remote of the instrument 10.

Figure 6:
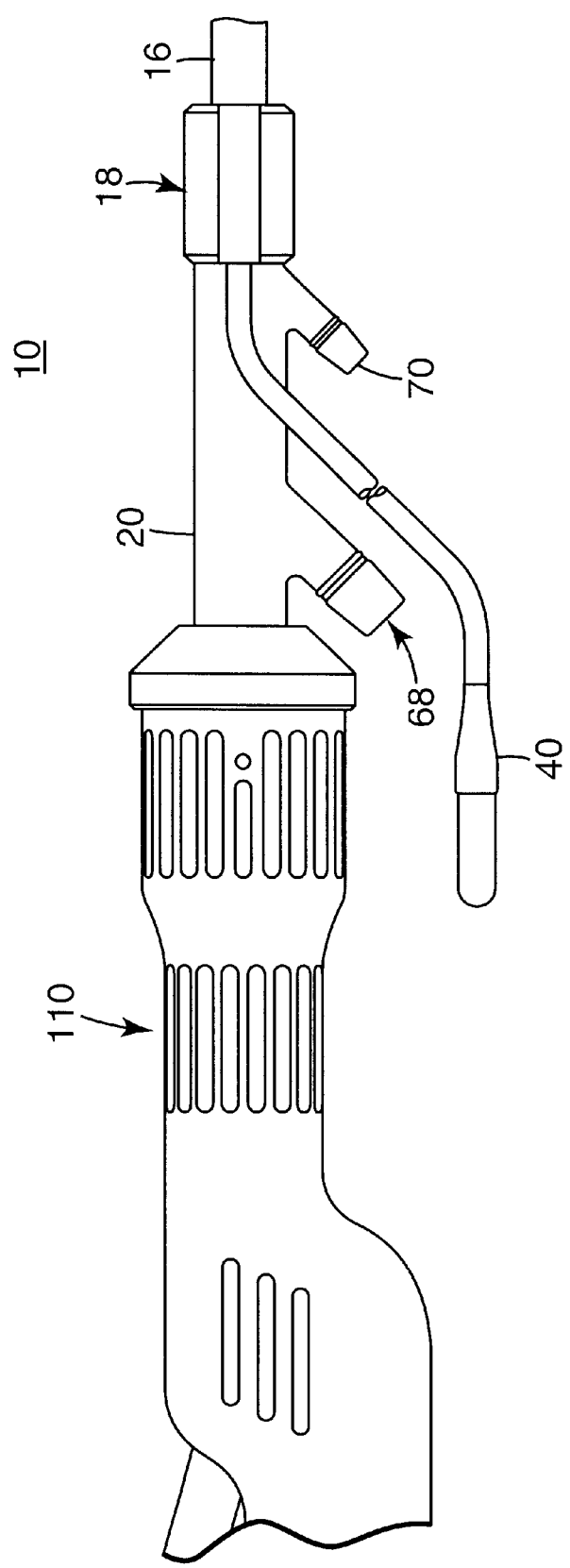
FIG. 6 is a side view of the surgical instrument of FIG. 1 assembled to a handpiece.

The surgical resecting instrument 10 is shown in conjunction with a removable powered surgical handpiece 110 in FIG. 6. The surgical handpiece 110 is of a type commonly known in the art and, as previously described, is selectively removable from the surgical resecting instrument 10. As illustrated in FIG. 6, the wire conductor 40, the aspiration port 68 and the irrigation port 70 are all external the surgical handpiece 110 upon assembly thereto. With this construction, then, the surgical handpiece 110 is electrically isolated or insulated from the surgical resecting instrument 10. This is an important feature as the handpiece 110 is typically metallic, and the presence of liquid (for irrigation) and electricity (for cauterizing) could result in a current being applied to the metallic handpiece and thus to the surgeon. Thus, it is necessary to isolate the handpiece 110 from the instrument 10.

During use, and with additional reference to FIG. 2, the surgical micro-resecting instrument 10 is deployed to a target site as with other cutting instruments. The cutting tip 86 of the inner tubular member 22 is maneuvered relative to the cutting window 34 to resect tissue at the target site, similar to conventional micro-resecting instruments. In this regard, and is known in the art, the inner tubular member 22 can be rotated and/or oscillated relative to the outer tubular member 16, for example, via operation of the surgical handpiece 110. When it becomes necessary to provide homostasis at the target site (either during or separate from cutting), an electrical current is applied to the outer tubular member 16 via the wire conductor 40. In a preferred embodiment, a radio frequency (RF) energy is employed on a monopolar basis. As a general statement, a monopolar electrosurgical instrument includes an active electrode (i.e., the teeth 36 of the outer tubular member 16) for cutting tissue and a remotely located return electrode for providing a return current path. For example, a remote ground pad, serving as the return electrode can be attached to the patient's body, such as the thigh or back. The cutting surface 36 serves as an electrode, cauterizing the contacted tissue to provide homostasis. Thus, the micro-resecting instrument 10 is highly useful for ENT procedures in which tissue is resected by cutting tip 86.

Figure 7:
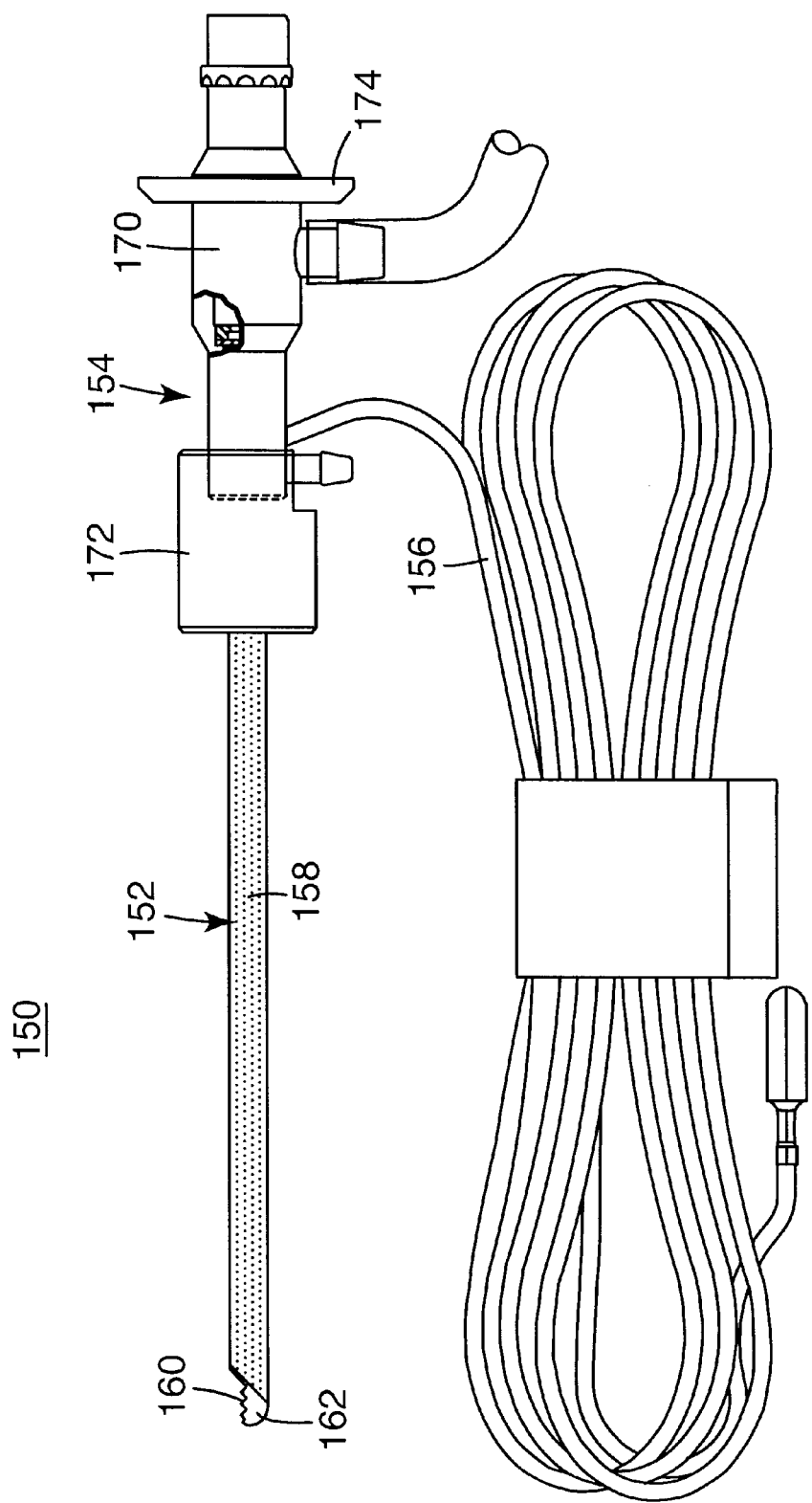
FIG. 7 is a side view of an alternative embodiment micro-resecting instrument in accordance with the present invention.

An alternative embodiment surgical micro-resecting instrument 150 particularly useful with ENT procedures requiring resecting of tissue is shown in FIG. 7. As with the previously-described instrument 10 (FIG. 1), the instrument 150 includes an outer tubular member 152, an inner tubular member (hidden in FIG. 7), a hub assembly 154, wiring 156, and an electrical insulator 158. The outer tubular member 152 forms a cutting window 160 at a distal portion thereof. The inner tubular member is coaxially disposed within the outer tubular member 152 and forms a cutting tip (not shown) otherwise exposed through the cutting window 160. The wiring 156 is electrically connected to the outer tubular member 152 at a connection point (not shown) otherwise encompassed by the hub assembly 154. That is to say, in accordance with a preferred embodiment, the hub assembly 154 ensures a permanent electrical connection between the wiring 156 and the outer tubular member 152 such that in a preferred embodiment, no switch mechanism is provided on the instrument 150.

The insulator 158 covers a region of the outer tubular member 152 distal the hub assembly 154. With the one preferred embodiment of FIG. 7, the cutting window 160 is not encompassed by, or is otherwise free of or exposed relative to, the insulator 158. Further, an exterior surface 162 (referenced generally in FIG. 7) of the outer tubular member 152 that otherwise surrounds and is opposite of the cutting window 160 is also exposed relative to the insulator 158. As previously described, energy provided to the wiring 156 by a separate power source is electrically delivered to the outer tubular member 152. The insulator 158, in turn, electrically insulates the outer tubular member 152 distal the hub assembly 154 except at the exposed surface 162. Thus, the exposed surface 162 is available for cauterizing contacted tissue.

The hub assembly 154 includes an outer hub 170, an inner hub (not shown), a cap 172, and a shroud 174. As with previous embodiments, the outer hub 170 is connected to a proximal section (not shown) of the outer tubular member 152. Similarly, the inner hub is connected to the inner tubular member (not shown), and is otherwise received within the outer hub 170. The cap 172 provides a transition region from the outer hub 170 to the outer tubular member 152, and covers a point of connection between the wiring 156 and the outer tubular member 152 as previously described. Finally, the shroud 174 extends in a generally radial fashion from the outer hub 170. The shroud 174 is preferably ring-shaped, and is formed of a non-conductive material such as ABS. With this configuration, the shroud 174 serves to impede or obstruct contact between components of the instrument 150 (or other components connected thereto) proximal the shroud 174 with other implements, bodily structures, etc. distal the shroud 170, during a surgical procedure, and in particular an electrocautery operation. For example, many ENT procedures are performed through a patient's mouth. With this technique, a mouth gag is commonly employed. Many mouth gags are formed of a metallic material. As such, the opportunity exists for the metallic mouth gag to come into contact with metallic components of the instrument 150 and/or associated micro-resecting system components (such as a powered handpiece). Metal-to-metal contact between the mouth gag (or other electrically conductive implement placed in or on the patient as part of the surgical procedure) and an instrument system component during an electrocautery operation could unexpectedly create an electrical pathway, potentially harming the patient or the instrument 150. The shroud 174 obstructs or prevents this undesirable contact from occurring by effectively preventing metallic components proximal the shroud 174 from contacting metallic implements distal the shroud 174. Notably, in a preferred embodiment, the shroud 174 is positioned such that all exposed surfaces of the instrument 150 distal the shroud 174 are electrically non-conductive, except for the surface 162. In one preferred embodiment, the shroud 174 has an outer diameter of approximately 0.875 inch.

Figure 8A:
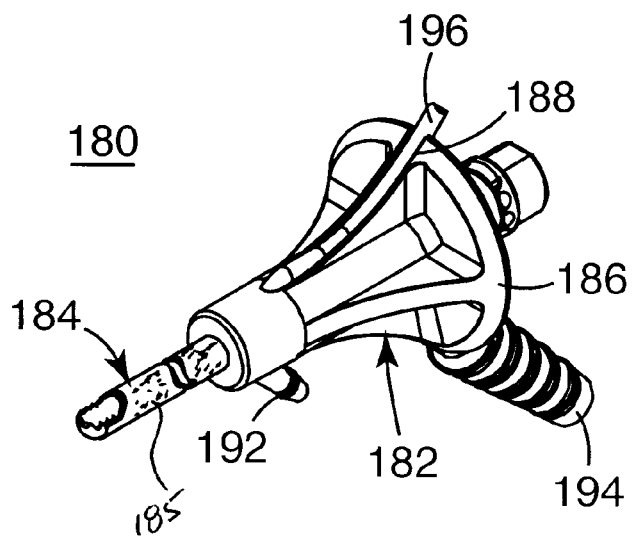
FIG. 8A is a perspective view of a portion of another alternative embodiment instrument in accordance with the present invention.
Figure 8B:
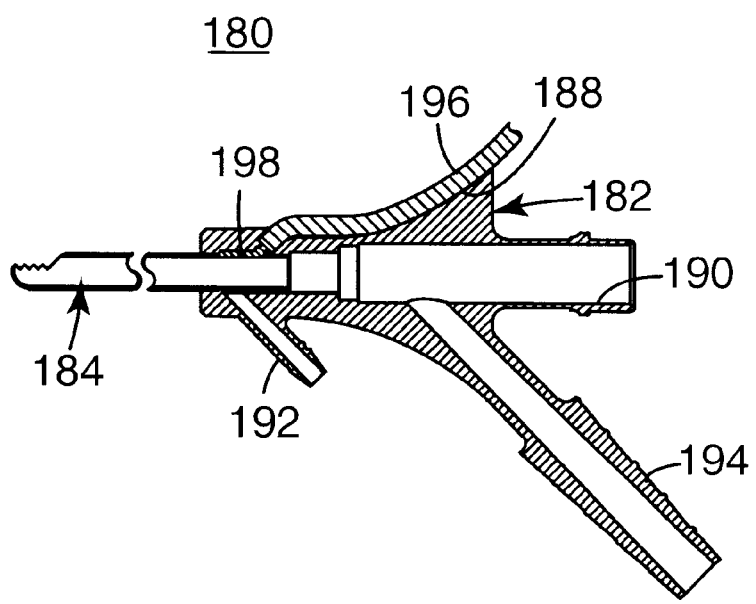
FIG. 8B is a cross-sectional view of the instrument of FIG. 8A.

The above-described hub assembly 154 (as well as the hub assembly associated with the instrument 10 previously described) incorporates individually formed outer hub and cap components that are separately secured to the outer tubular member. Alternatively, FIGS. 8A and 8B illustrate an alternative embodiment micro-resecting instrument 180 incorporating an insert molded outer hub 182. The outer hub 182 is insert molded to an outer tubular member 184. An insulator 185 encompasses a region of the outer tubular member 184 distal the outer hub 182. In accordance with one preferred embodiment, the outer hub 182 is molded to form a shroud portion 186, a wire receiving groove 188, a central lumen 190, an irrigation port 192, and an aspiration port 194. The shroud 186 is configured to prevent metallic components proximal the shroud 186 from contacting metallic implements distal the shroud 186 during a surgical procedure, similar to the shroud 174 (FIG. 7) previously described.

As with previous embodiments, the micro-resecting instrument 180 includes wiring 196 that is electrically connected to the outer tubular member 184 as best shown in FIG. 8B. In this regard, the outer hub 182 is molded over a connection point 198 between the wiring 196 and the outer tubular member 184. Further, the wire-receiving groove 188 is adapted to maintain a portion of the wiring 196 proximal the connection point 198.

The surgical micro-resecting instrument of the present invention provides a marked improvement over previous designs by providing a single instrument capable of micro-resecting and providing homostasis, for example by electrocautery. By covering a substantial portion of the outer tubular member with an electrical insulator, as well as providing external aspiration, the surgical instrument of the present invention greatly reduces the surgical time by providing a single device capable of performing multiple tasks while eliminating the possibility of malfunction or injury (due to the metallic nature of most handpieces).

Although the present invention has been described with reference to preferred embodiments, workers skilled in the art will recognize that changes can be made in form and detail without departing from the spirit and scope of the present invention. For example, while the insulator has been described as encompassing an entirety of the outer tubular member except for the cutting window, it will be understood that additional regions of the distal section of the outer tubular member can also be left exposed.

What is claimed is:

1. A surgical micro-resecting instrument for use with an ENT procedure, the instrument comprising:

an outer tubular member formed of an electrically conductive material and defining a proximal section, an intermediate section, a distal section, and an internal lumen, wherein the distal section forms a cutting window open to the lumen;

an inner tubular member disposed within the lumen of the outer tubular member, the inner tubular member defining a proximal end and a distal end, wherein the distal end forms a cutting tip;

a hub assembly maintaining the outer tubular member at the proximal section thereof and the inner tubular member at the proximal end thereof;

wiring permanently electrically connected to the proximal section of the outer tubular member and adapted to deliver energy to the outer tubular member from a remote power source, wherein the electrical connection of the wiring to the outer tubular member is encompassed by the hub assembly; and an electrical insulator covering a region of the outer tubular member distal the hub assembly, wherein the cutting window is free of the insulator.

2. The instrument of claim 1, the cutting window is defined by a cutting surface, and further wherein the cutting surface is the only portion of the distal section not covered by the insulator.

3. The instrument of claim 1, wherein the region of the outer tubular member covered by the insulator does not include an exterior surface of the distal section otherwise surrounding the cutting window.

4. The instrument of claim 1, wherein at least a portion of an exterior surface of the distal section of the outer tubular member opposite the cutting window is not encompassed by the insulator.

5. The instrument of claim 1, wherein the insulator is a dielectric material coated onto the outer tubular member.

6. The instrument of claim 5, wherein the proximal section of the outer tubular member is not coated with the dielectric material.

7. The instrument of claim 1, wherein the hub assembly includes:
an outer hub connected to the proximal section of the outer tubular member; and
an inner hub connected to the proximal end of the inner tubular member, wherein the inner hub is received within the outer hub and includes a proximal section adapted to releasably engage a powered surgical handpiece.

8. The instrument of claim 7, wherein the inner hub is fluidly sealed to the outer hub.

9. The instrument of claim 7, wherein the inner hub forms a radial passage in fluid communication with a longitudinal passage otherwise adapted to receive the proximal end of the inner tubular member, and further wherein upon final assembly, the radial passage is fluidly connected to a fluid port formed by the outer hub.

10. The instrument of claim 7, wherein the hub assembly further includes a cap disposed over a portion of the outer tubular member and a portion of the outer hub, the cap adapted to cover the connection between the wiring and the outer tubular member.

11. The instrument of claim 7, wherein the hub assembly further includes:
a shroud extending in a generally radial fashion from the outer hub, the shroud adapted to obstruct contact between a patient and a component proximal the shroud.

12. The instrument of claim 7, wherein the outer hub is insert molded to the outer tubular member.

13. The instrument of claim 12, wherein the outer hub is molded over the connection between the wiring and the proximal section of the outer tubular member.

14. The instrument of claim 12, wherein the outer hub is molded to define a fluid port.

15. The instrument of claim 12, wherein the outer hub is molded to define a groove sized to maintain a portion of the wiring proximal the connection between the wiring and the outer tubular member.

16. The instrument of claim 12, wherein the outer hub is molded to define a generally radially extending shroud adapted to obstruct contact between a patient and a component proximal the shroud.

17. A surgical micro-resecting system comprising:
a micro-resecting instrument including:
an outer tubular member formed of an electrically conductive material and defining a proximal section, an intermediate section, a distal section, and an internal lumen, wherein the distal section forms a cutting window open to the lumen,
an inner tubular member disposed within the lumen and defining a proximal end and a distal end, wherein the distal end forms a cutting tip,
a hub assembly maintaining the outer tubular member at the proximal section thereof and the inner tubular member at the proximal end thereof,
wiring permanently electrically connected to the proximal section of the outer tubular member, wherein electrical connection of the wiring to the outer tubular member is encompassed by the hub assembly,
an electrical insulator covering a region of the outer tubular member distal the hub assembly, wherein the cutting window is free of the insulator;
a powered surgical handpiece coupled to the proximal end of the tubular member for driving the inner tubular member relative to the outer tubular member; and
an energy source electrically connected to the wiring opposite the outer tubular member.

18. The system of claim 17, further comprising:
a foot switch electrically connected to the powered surgical handpiece for controlling operation thereof;
wherein the system is characterized by the absence of a power control mechanism on the micro-resecting instrument.

19. The system of claim 17, further comprising:
a fluid source fluidly connected to the hub assembly;
a vacuum source fluidly connected to the hub assembly;
wherein the hub assembly fluidly connects the fluid source to the internal lumen of the outer tubular member and the vacuum source to a lumen of the inner tubular member.

20. The system of claim 17, wherein the cutting window is defined by a cutting surface, and further wherein the cutting surface is the only portion of the distal section not covered by the insulator.

21. The system of claim 17, wherein at least a portion of an exterior surface of the distal section of the outer tubular member opposite the cutting window is not encompassed by the insulator.

22. The system of claim 17, wherein the insulator is a dielectric material coated onto the outer tubular member.

23. The system of claim 17, wherein the hub assembly includes:
an outer hub connected to the proximal section of the outer tubular member; and
an inner hub connected to the proximal end of the inner tubular member, wherein the inner hub is received within the outer hub and includes a proximal section adapted to releasably engage a powered surgical handpiece.

24. The system of claim 23, wherein the hub assembly further includes a cap disposed over a portion of the outer tubular member and a portion of the outer hub, the cap adapted to cover the connection between the wiring and the outer tubular member.

25. The system of claim 23, wherein the hub assembly further includes:
a shroud extending in a generally radial fashion from the outer hub, the shroud adapted to obstruct contact between a patient and a component proximal the shroud.

26. The system of claim 23, wherein the outer hub is insert molded to the outer tubular member.

27. The system of claim 26, wherein the outer hub is molded over the connection between the wiring and the proximal section of the outer tubular member.

28. The system of claim 26, wherein the outer hub is molded to define a generally radially extending shroud adapted to obstruct contact between a patient and a component proximal the shroud.

29. A method for performing a micro-resecting operation at a target site of a patient as part of an ENT surgical procedure, the method comprising:
providing a micro-resecting instrument including an outer tubular member having a lumen and a distal section forming a cutting window open to the lumen, an inner tubular member disposed within the lumen and having a distal end forming a cutting tip, wiring permanently electrically connected at a connection point to a proximal section of the outer tubular member, a hub assembly maintaining the inner and outer tubular members and enveloping the connection point, and an electrical insulator covering a region of the outer tubular member distal the hub assembly such that at least the cutting window remains exposed relative to the insulator;
delivering the distal section of the outer tubular member to the target site such that the cutting window is located at the target site and the cutting tip is located within the cutting window;
driving the inner tubular member relative to the outer tubular member such that the cutting tip resects tissue at the target site to effectuate a portion of an ENT procedure;
supplying energy to an exposed region of the distal section of the outer tubular member via the wiring; and
cauterizing tissue at the target site via the energized exposed region.

30. The method of claim 29, further comprising:
prompting supply of energy to the outer tubular member by interfacing with an energy control device remote of the micro-resecting instrument.

31. The method of claim 30, wherein the energy control device includes a switch mechanism located remote of the micro-resecting instrument.

32. The method of claim 30, wherein prompting supply of energy is characterized by the absence of direct user interface with the micro-resecting instrument.

33. The method of claim 29, wherein providing a micro-resecting instrument includes providing the micro-resecting instrument with a shroud extending in a generally radial fashion as part of the hub assembly, and further wherein delivering the distal section to the target site includes:
grasping the hub assembly proximal the shroud.

34. The method of claim 33, further comprising:
locating a metallic component on the patient as part of an ENT procedure prior to the step of delivering the distal section to the target site, the metallic component being positioned in a region coinciding with a delivery path of the micro-resecting instrument;
wherein the shroud prevents contact between the metallic component and portions of the micro-resecting instrument proximal the shroud during the step of supplying energy to the outer tubular member.

35. The method of claim 34, wherein the metallic component is a mouth gag.

36. The method of claim 29, further comprising:
selectively coupling the micro-resecting instrument to a powered surgical handpiece.

37. The method of claim 29, wherein driving the inner tubular member includes depressing a foot switch remote of the micro-resecting instrument.

38. A method of manufacturing a micro-resecting instrument for use in an ENT procedure, the method comprising:
providing an outer tubular member formed of an electrically conductive material and including a proximal section, a distal section, and a lumen, the distal section forming a cutting window open to the lumen;
providing an inner tubular member having a proximal end and a distal end, the distal end forming a cutting tip;
disposing the inner tubular member within the lumen such that the cutting tip is aligned with the cutting window;
electrically connecting wiring to the proximal section of the outer tubular member;
connecting a hub assembly to the proximal section of the outer tubular member and the proximal end of the inner tubular member, the hub assembly encompassing the connection between the wiring and the outer tubular member such that the wiring is permanently electrically connected to the outer tubular member; and
covering a region of the outer tubular member distal the hub assembly with an electrical insulator, at least the cutting window being exposed relative to the insulator.

39. The method of claim 38, wherein covering a region of the outer tubular member with the insulator includes covering an entirety of the outer tubular member distal the hub assembly except for the cutting window.

40. The method of claim 38, wherein covering a region of the outer tubular member with the insulator includes leaving at least a portion of an exterior surface of the distal section opposite the cutting window exposed relative to the insulator.

41. The method of claim 38, wherein covering a region of the outer tubular member with an insulator includes coating the region with a dielectric material.

42. The method of claim 38, further comprising:
providing the hub assembly to include an inner hub for connection to the inner tubular member and an outer hub for connection to the outer tubular member, the inner hub including a proximal section adapted to releasably engage a powered surgical handpiece.

43. The method of claim 42, wherein the outer hub forms a lumen and a fluid port, and the inner hub forms a radial passage fluidly connected to a longitudinal passage, and further wherein connecting the hub assembly includes fluidly connecting the radial passage of the inner hub to the fluid port of the outer hub.

44. The method of claim 42, wherein providing the hub assembly further includes forming a shroud extending in a generally radial fashion from the outer hub.

45. The method of claim 42, wherein connecting the hub assembly includes insert molding the outer hub to the outer tubular member.

46. The method of claim 45, wherein insert molding the outer hub includes molding the outer hub over the connection between the wiring and the outer tubular member.

47. The method of claim 45, wherein insert molding the outer hub includes molding the outer hub to form a groove sized to maintain a portion of the wiring proximal the connection between the wiring and the outer tubular member.

48. The method of claim 45, wherein insert molding the outer hub includes molding the hub to define a generally radially extending shroud.

49. The method of claim 38, wherein the method of manufacture is characterized by the absence of any external switch device on the micro-resecting instrument.

50. A surgical micro-resecting instrument for use with an ENT procedure, the instrument comprising:

an outer tubular member formed of an electrically conductive material and defining a proximal section, an intermediate section, a distal section, and an internal lumen, wherein the distal section forms a cutting window open to the lumen;

an inner tubular member disposed within the lumen of the outer tubular member, the inner tubular member defining a proximal end and a distal end, wherein the distal end forms a cutting tip;

a hub assembly including:
   an outer hub connected to the proximal section of the outer tubular member,
   an inner hub connected to the proximal end of the inner tubular member, wherein the inner hub is received within the outer hub and includes a proximal section adapted to releasably engage a powered surgical handpiece;

wiring electrically connected to the proximal section of the outer tubular member and adapted to deliver energy to the outer tubular member from a remote power source, wherein the electrical connection of the wiring to the outer tubular member is encompassed by the hub assembly; and an electrical insulator covering a region of the outer tubular member distal the hub assembly, wherein the cutting window is free of the insulator.

* * * * *